(12) United States Patent
Matoba

(10) Patent No.: US 7,623,627 B2
(45) Date of Patent: Nov. 24, 2009

(54) X-RAY ANALYSIS APPARATUS AND X-RAY ANALYSIS METHOD

(75) Inventor: Yoshiki Matoba, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 12/369,062

(22) Filed: Feb. 11, 2009

(65) Prior Publication Data

US 2009/0213996 A1    Aug. 27, 2009

(30) Foreign Application Priority Data

Feb. 22, 2008   (JP) ............................... 2008-042242

(51) Int. Cl.
*G01N 23/201* (2006.01)
(52) U.S. Cl. ............................... 378/87; 378/58; 378/86
(58) Field of Classification Search .................... 378/57, 378/58, 63, 86, 87, 88–90
See application file for complete search history.

(56) References Cited

U.S. PATENT DOCUMENTS 7,492,863 B2 *  2/2009  Harding ........................ 378/71
2009/0147920 A1 *  6/2009  Barty et al. .................... 378/88

FOREIGN PATENT DOCUMENTS

JP    2007-292476 A    11/2007

* cited by examiner

*Primary Examiner*—Hoon Song
(74) *Attorney, Agent, or Firm*—Brinks Hofer Gilson & Lione

(57) ABSTRACT

Provided are an X-ray analysis apparatus and an X-ray analysis method, in which a measurer can judge an area incapable of being analyzed in a sample with a concave-convex portion. The X-ray analysis apparatus includes: an X-ray tubular bulb for irradiating an arbitrary irradiation point located on the sample with a radiation beam; an X-ray detector for detecting a characteristic X-ray and a scattered X-ray radiated from the sample and outputting a signal containing energy information on the characteristic X-ray and the scattered X-ray; a narrow-range illumination mechanism and a wide-range illumination mechanism for emitting an illumination light to the sample to illuminate the sample; and a narrow-range observation mechanism and a wide-range observation mechanism for obtaining an illumination image of the sample, which is illuminated with the illumination light, as image data, in which the narrow-range observation mechanism and the wide-range observation mechanism include a narrow-range oblique illumination section and a wide-range oblique illumination section, respectively, in which an optical axis of the illumination light at a time of the illuminating is set toward the irradiation point in the same direction as a direction linking the irradiation point with the X-ray detector at a time of the detecting.

6 Claims, 2 Drawing Sheets

X-RAY ANALYSIS APPARATUS AND X-RAY ANALYSIS METHOD

RELATED APPLICATIONS

This application claims priority under 35 U.S.C. §119 to Japanese Patent Application No. JP2008-042242 filed on Feb. 22, 2008, the entire content of which is hereby incorporated by reference.

BACKGROUND

1. Field of the Invention

The present invention relates to an X-ray analysis apparatus and an X-ray analysis method which are suitable for, for example, an energy dispersive fluorescent X-ray analysis.

2. Description of the Related Art

In a fluorescent X-ray analysis, an X-ray emitted from an X-ray source is irradiated to a sample, and a fluorescent X-ray which is a characteristic X-ray radiated from the sample is detected by an X-ray detector, whereby a spectrum is obtained from energy of the fluorescent X-ray for performing a qualitative analysis or a quantitative analysis of the sample. The fluorescent X-ray analysis is widely used in a process and quality control because it is possible to rapidly analyze the sample in a nondestructive manner in the fluorescent X-ray analysis. In recent years, there has been contrived to increase precision and sensitivity thereof, which enables a trace measurement. Accordingly, there is expected the diffusion of the X-ray analysis as an analysis technique of performing especially a detection of a harmful substance contained in a material, a composite electronic component, or the like.

As the analysis technique of the fluorescent X-ray analysis, for example, there is provided a wavelength dispersion method in which the fluorescent X-ray is dispersed by a spectral crystal to thereby measure a wavelength and intensity of the X-ray, or an energy dispersion method in which the fluorescent X-ray is detected by a semiconductor detection element without being dispersed to thereby measure energy and intensity of the X-ray by a pulse height analyzer.

Conventionally, for example, JP 2007-292476 A discloses an X-ray analysis apparatus which includes an X-ray source for irradiating an X-ray and an optical microscope for observing an analysis point of a sample, and switches between the X-ray source and the optical microscope to obtain the same optical axis therebetween. In the X-ray analysis apparatus, the sample can be subjected to optical observation by the optical microscope to identify an analysis position or a shape of the sample can be measured while the sample is being mounted on a sample stage.

However, the above-mentioned conventional technology has the following problems.

That is, in the conventional X-ray analysis apparatus, in a case where a sample having a concave-convex portion is subjected to pinpoint analysis, as illustrated in FIG. 4, when a convex portion S1 of a sample S exists between an X-ray detector 2 and an irradiation point (that is, analysis point) P to which a radiation beam X0 such as an excited X-ray on a primary side (primary X-ray) or an excited electron beam is irradiated from a radiation source 1, an X-ray X2 generated at the irradiation point P is absorbed by the convex portion S1 and does not reach the X-ray detector 2. Accordingly, X-ray analysis cannot be performed in a region of the irradiation point P. Further, in the conventional X-ray analysis apparatus, the sample mounted on the sample stage is observed from thereabove with the optical microscope or the like, but observation is performed in a similar direction as that of the X-ray source, and hence it is difficult to specify an area incapable of being analyzed due to the concave-convex portion or the like.

SUMMARY OF THE INVENTION

The present invention has been made in view of the above-mentioned problems, and therefore an object thereof is to provide an X-ray analysis apparatus and an X-ray analysis method, in which a measurer can judge an area incapable of being analyzed in a sample having a concave-convex portion.

In order to solve the above-mentioned problems, the present invention adopts the following configuration. That is, an X-ray analysis apparatus according to the present invention includes: a radiation source for irradiating an arbitrary irradiation point located on a sample with a radiation beam; an X-ray detector for detecting a characteristic X-ray and a scattered X-ray radiated from the sample and outputting a signal containing energy information on the characteristic X-ray and the scattered X-ray; an illumination mechanism for emitting an illumination light to the sample to illuminate the sample; and an observation mechanism for obtaining an illumination image of the sample, which is illuminated with the illumination light, as image data, in which the illumination mechanism includes a concave-convex illumination section in which an optical axis of the illumination light at a time of the illuminating is set toward the irradiation point in the same direction as a direction linking the irradiation point with the X-ray detector at a time of the detecting.

Further, according to the present invention, an X-ray analysis method of irradiating an arbitrary irradiation point located on a sample with a radiation beam by a radiation source, detecting a characteristic X-ray and a scattered X-ray radiated from the sample by an X-ray detector, and outputting a signal containing energy information on the characteristic X-ray and the scattered X-ray, the X-ray analysis method includes: illuminating the sample by emitting an illumination light to the sample by an illumination mechanism before irradiating with the radiation beam; and obtaining an illumination image of the sample, which is illuminated with the illumination light, as image data by an observation mechanism, in which the illuminating the sample includes setting an optical axis of the illumination light at a time of the illuminating toward the irradiation point in the same direction as a direction linking the irradiation point with the X-ray detector at a time of the detecting by a concave-convex illumination section included in the illumination mechanism, to illuminate the sample.

In the X-ray analysis apparatus and the X-ray analysis method, the illumination mechanism includes the concave-convex illumination section in which the optical axis of the illumination light at the time of the illuminating is set toward the irradiation point in the same direction as the direction linking the irradiation point with the X-ray detector at the time of the detecting, and hence a shadow portion corresponding to a concave-portion convex of the sample can be generated through illumination of the concave-convex illumination section and specified as an area incapable of being analyzed. In other words, the shadow portion is nearly equal to the area incapable of being analyzed in which the X-ray generated at the irradiation point at the time of the detecting cannot reach the X-ray detector due to the concave-convex portion. Even when the shadow portion is provided to the measurer as a visible light image, the area incapable of being analyzed can be specified without difficulty. Moreover, in the case where the X-ray is inappropriately detected due to the concave-convex portion of the sample, the measurer becomes capable of easily judging through the specification of the area incapable of being analyzed that a measurement result becomes inappropriate because of a decrease in signal amount of the X-ray, with the result that erroneous determination can be prevented.

Further, the X-ray analysis apparatus according to the present invention further includes a shadow portion specification processing section for identifying a shadow portion generated by the illumination light of the concave-convex illumination section as the area incapable of being analyzed through image processing based on a concave-convex image, and outputting a position thereof as information on the area incapable of being analyzed, in which the observation mechanism records the illumination image of the sample, which is illuminated with the illumination light of the concave-convex illumination section, as the concave-convex image. Specifically, in the X-ray analysis apparatus, the shadow portion specification processing section identifies the shadow portion generated by the illumination light through the image processing based on the concave-convex image as the area incapable of being analyzed and outputs the position thereof as the information on the area incapable of being analyzed, whereby an image of the shadow portion is recognized and automatically identified to be specified through the image processing. Moreover, various kinds of analysis processing or analysis operations can be made based on the output information on the area incapable of being analyzed.

Further, in the X-ray analysis apparatus according to the present invention, the illumination mechanism includes a reference illumination section in which the optical axis of the illumination light at the time of the illuminating is set toward the irradiation point in the same direction as an irradiation direction of the radiation beam at the time of the detecting; the observation mechanism records the illumination image of the sample, which is illuminated with the illumination light of the reference illumination section, as a reference image; and the shadow portion specification processing section identifies the area incapable of being analyzed through image processing in which the concave-convex image is compared with the reference image. Specifically, in the X-ray analysis apparatus, the shadow portion specification section identifies the area incapable of being analyzed through the image processing such as difference processing in which the concave-convex images generated by the concave-convex illumination sections which have illumination different from each other with the reference image generated by the reference illumination section. Accordingly, the area incapable of being analyzed can be identified more accurately.

Further, the X-ray analysis apparatus according to the present invention further includes a warning mechanism when the irradiation point is set in the area incapable of being analyzed. Specifically, in the X-ray analysis apparatus, the warning mechanism displays warning or generates a warning beep based on the information on the area incapable of being analyzed if the irradiation point is set in the area incapable of being analyzed to be measured. Therefore, the measurer does not need to perform unnecessary analysis operation for the area incapable of being analyzed, which makes it possible to perform the analysis operation efficiently. As to the area incapable of being analyzed in which the warning is displayed or the warning beep is generated, it is also possible to take a measure in which a direction of the sample or the like is changed and reset to be measured again.

Further, the X-ray analysis apparatus according to the present invention further includes: a moving mechanism capable of relatively moving a position of the sample and a position of the concave-convex illumination section; and a detection direction control section for controlling the moving mechanism, when the irradiation point is set in the area incapable of being analyzed, based on the information on the area incapable of being analyzed, to change a detection direction of the X-ray detector with respect to the sample into a direction in which the irradiation point becomes a portion other than the shadow portion. Specifically, in the X-ray analysis apparatus, the detection direction control section controls the moving mechanism based on the information on the area incapable of being analyzed to relatively change a positional relationship between the sample and the x-ray detector into the direction in which the irradiation point does not become the shadow portion, with the result that a point which has been the shadow portion can be automatically measured through change of the positional relationship between the sample and the X-ray detector.

According to the present invention, the following effects can be achieved.

That is, in the X-ray analysis apparatus and the X-ray analysis method according to the present invention, the illumination mechanism includes the concave-convex illumination section in which the optical axis of the illumination light at the time of the illuminating is set toward the irradiation point in the same direction as the direction linking the irradiation point with the X-ray detector at the time of the detecting, with the result that the shadow portion corresponding to the concave-convex portion of the sample can be generated through illumination of the concave-convex illumination section and specified as the area incapable of being analyzed. Accordingly, the measurer can easily judge the area incapable of being analyzed, which enhances the reliability of an analysis result and also prevents, for example, redoing analysis.

DETAILED DESCRIPTION OF THE PREFERRED EMBODIMENTS

Hereinafter, an embodiment of an X-ray analysis apparatus and an X-ray analysis method according to the present invention is described with reference to FIG. 1 to FIG. 3.

Figure 1:
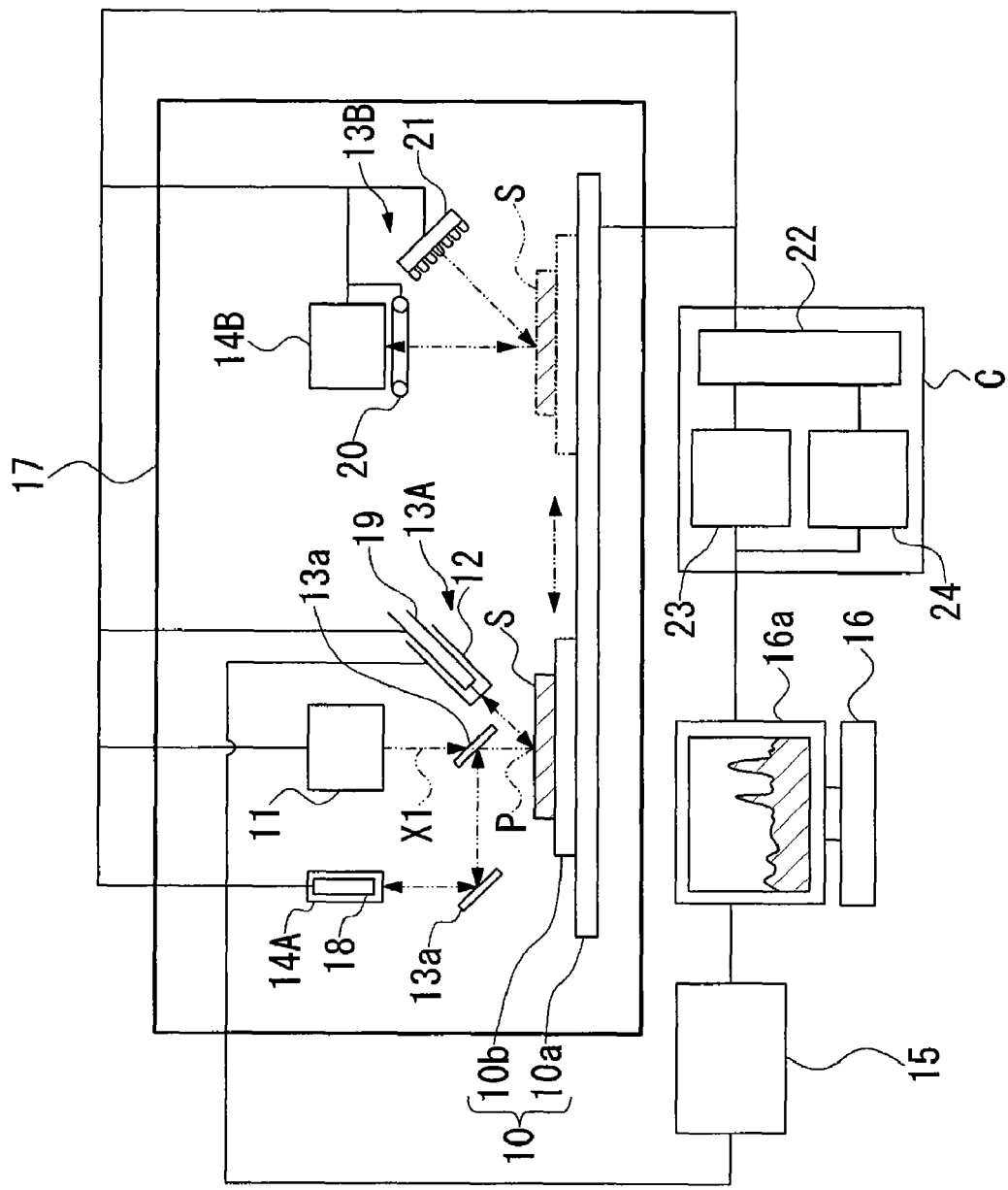
FIG. 1 is an entire configuration diagram schematically illustrating an X-ray analysis apparatus and an X-ray analysis method according to an embodiment of the present invention.

The X-ray analysis apparatus according to this embodiment is, for example, an energy dispersive fluorescent X-ray analysis apparatus, and as illustrated in FIG. 1, includes a movable sample stage 10 for mounting a sample S thereon, an X-ray tubular bulb (radiation source) 11 for irradiating a primary X-ray (radiation beam) X1 to an arbitrary irradiation point P located on the sample S, an X-ray detector 12 for detecting a characteristic X-ray and a scattered X-ray which are radiated from the sample S and outputting a signal containing energy information on the characteristic X-ray and the scattered X-ray, a narrow-range illumination mechanism 13A and a wide-range illumination mechanism 13B for emitting illumination light to the sample S for illumination, a narrow-range observation mechanism 14A and a wide-range observation mechanism 14B for obtaining an illumination image of the sample S irradiated with the illumination light as image data, an analyzer 15 connected with the X-ray detector 12 for analyzing the signal, an analysis processing device 16 connected to the analyzer 15, and a control section C connected to the above-mentioned components for controlling those components.

The X-ray tubular bulb 11 emits as the primary X-ray X1 an X-ray, which is generated by the fact that thermoelectrons generated from a filament (positive electrode) of the tubular bulb are accelerated by a voltage applied between the filament (positive electrode) and a target (negative electrode) to thereby impinge against the target of W (tungsten), Mo (molybdenum), Cr (chromium), or the like, from a window of a beryllium foil or the like.

The X-ray detector 12 includes a semiconductor detection element (for example, Si (silicon) element which is a pin-structure diode) (not shown) disposed to an incident window of the X-ray, and when one X-ray photon enters, generates a current pulse corresponding to the one X-ray photon. A momentary current value of the current pulse is proportional to energy of the characteristic X-ray which enters. Further, the X-ray detector 12 is set so as to convert the current pulse generated in the semiconductor detection element into a voltage pulse, amplify the voltage pulse, and output the amplified voltage pulse as a signal.

The analyzer 15 is a pulse height analyzer (multichannel pulse-height analyzer) for obtaining a pulse height of the voltage pulse from the signal, thereby generating an energy spectrum.

The analysis processing device 16 is a computer configured by a CPU and the like, and displays the energy spectrum sent from the analyzer 15 on a display 16a. It should be noted that the control section C may be provided in a processing circuit of the analysis processing device 16. Moreover, the display 16a can display various items of information in accordance with control of the control section C.

The sample stage 10, the X-ray tubular bulb 11, the X-ray detector 12, the narrow-range illumination mechanism 13A, the wide-range illumination mechanism 13B, the narrow-range observation mechanism 14A, and the wide-range observation mechanism 14B are accommodated in a sample chamber 17 which is capable of being decompressed. When measurement is performed, the sample chamber 17 is decompressed in order to prevent the X-ray from being absorbed to an atmosphere in the air.

The narrow-range observation mechanism 14A is provided in the vicinity of positions at which the X-ray tubular bulb 11 and the X-ray detector 12 are provided, and includes a narrow-range objective lens (not shown) and a narrow-range CCD (not shown) for observing an optical image of the sample S in a narrow range through a plurality of mirrors 13a and obtaining the optical image as image data.

The wide-range observation mechanism 14B is provided to be adjacent to the narrow-range observation mechanism 14A, and includes a wide-range objective lens (not shown) and a wide-range CCD (not shown) for observing an optical image of the sample S in a wide range and obtaining the optical image as image data.

The narrow-range illumination mechanism 13A illuminates a narrow range of the sample S when the narrow-range observation mechanism 14A performs observation, and the wide-range illumination mechanism 13B illuminates a wide range of the sample S when the wide-range observation mechanism 14B performs observation.

The narrow-range illumination mechanism 13A includes a coaxial illumination section (reference illumination section) 18 and a narrow-range oblique illumination section (concave-convex illumination section) 19. In the coaxial illumination section 18, an optical axis of illumination light at a time of illumination is set through the plurality of mirrors 13a in the same direction as irradiation direction of the primary X-ray X1 at a time of detection. In the narrow-range oblique illumination section 19, an optical axis of illumination light at a time of illumination is set toward the irradiation point P in the same direction as a direction linking the irradiation point P with the X-ray detector 12 at a time of detection.

It should be noted that, in order to illuminate the illumination light of the coaxial illumination section 18 to the sample S to be coaxial with the narrow-range observation mechanism 14A, the narrow-range illumination mechanism 13A includes the plurality of mirrors 13a as an optical system for illuminating the illumination light of the coaxial illumination section 18 from above the sample S in a direction perpendicular to the sample S. The mirror 13a provided directly below the X-ray tubular bulb 11 is set to be automatically movable to a retreat position at the time of detection so that the primary X-ray X1 can pass.

The narrow-range oblique illumination section 19 is a device which is placed on both sides of the X-ray detector 12 side-by-side to make a pair toward the same direction so that the optical axis of the illumination light is set to be substantially in the same direction as the detection direction of the X-ray detector 12, for illuminating the irradiation point P and a relatively narrow range therearound.

The wide-range illumination mechanism 13B includes a ring illumination section (reference illumination section) 20 and a wide-range oblique illumination section (concave-convex illumination section) 21. In the ring illumination section 20, the optical axis of the illumination light at the time of illumination is set toward the irradiation point P in the same direction as the irradiation direction of the primary X-ray X1 at the time of detection. In the wide-range oblique illumination section 21, the optical axis of the illumination light at the time of illumination is set toward the irradiation point P in the same direction as the direction linking the irradiation point P with the X-ray detector 12 at the time of detection.

The ring illumination section 20 is placed below the wide-range observation mechanism 14B for illuminating the illumination light from above the sample S in a direction perpendicular to the sample S.

The wide-range oblique illumination section 21 is an illumination device capable of illumination in a wide range by arranging a plurality of LEDs on a flat surface. An illumination direction (optical axis of the illumination light) of the wide-range oblique illumination section 21 is set to be parallel to the detection direction of the X-ray detector 12. Specifically, in the case where the detection direction of the X-ray detector 12 with respect to a surface of the sample S is 45 degrees, the illumination direction of the wide-range oblique illumination section 21 is also set to be parallel to the detection direction of the X-ray detector 12 and have 45 degrees with respect to the surface of the sample S. Accordingly, the wide-range oblique illumination section 21 is set so that the optical axis of the illumination light at the time of illumination is directed toward the irradiation point P in the same direction as the direction linking the irradiation point P with the X-ray detector 12 at the time of detection.

The narrow-range observation mechanism 14A and the wide-range observation mechanism 14B each have a function of taking the illumination images of the sample S illuminated with the illumination lights of the coaxial illumination section 18 and the ring illumination section 20 as a reference image with the use of the narrow-range CCD and the wide-range CCD and sending image data thereof to the control section C to be recorded, and also taking the illumination images of the sample S illuminated with the illumination lights of the narrow-range oblique illumination section 19 and the wide-range oblique illumination section 21 as a concave-convex image and sending image data thereof to the control section C to be recorded.

The sample stage 10 includes an XY stage section 10*a* capable of moving horizontally by means of a stepping motor (not shown) or the like in a state in which the sample S is fixed, and a rotatable stage section (moving mechanism) 10*b* capable of relatively moving in the illumination directions of the narrow-range oblique illumination section 19 and the wide-range oblique illumination section 21 with respect to the irradiation point P by rotating the sample S.

The control section C includes a shadow portion specification processing section 22, a warning mechanism 23, and a detection direction control section 24. The shadow portion specification processing section 22 identifies shadow portions generated by the illumination lights of the narrow-range oblique illumination section 19 and the wide-range oblique illumination section 21 as an area incapable of being analyzed based on the concave-convex image through image processing, and outputs positions thereof as information on the area incapable of being analyzed. The warning mechanism 23 displays warning or generates a warning beep based on the information on the area incapable of being analyzed when the irradiation point P is set in the area incapable of being analyzed. The detection direction control section 24 controls, when the irradiation point P is set in the area incapable of being analyzed, the sample stage 10 based on the information on the area incapable of being analyzed in the case of automatic setting, and changes a direction of the X-ray detector 12 with respect to the sample S into a direction in which the irradiation point P does not become the shadow portion.

The shadow portion specification processing section 22 has a function of identifying the area incapable of being analyzed through image processing in which the concave-convex image is compared with the reference image.

Next, the X-ray analysis method using the X-ray analysis apparatus according to this embodiment is described with reference to FIG. 1 to FIG. 3.

First, the sample S is set on the sample stage 10, and the sample chamber 17 is made to be in a predetermined decompressed state. Next, the sample stage 10 is driven to move the sample S directly below the wide-range observation mechanism 14B for performing wide-range observation. In this state, the sample S is illuminated from thereabove in a direction perpendicular thereto by means of the ring illumination section 20, and an illuminated sample image is obtained as wide-range reference image data by means of the wide-range observation mechanism 14B. The wide-range reference image data is sent to and recorded in the control section C, and is displayed on the display 16*a*.

Figure 2:
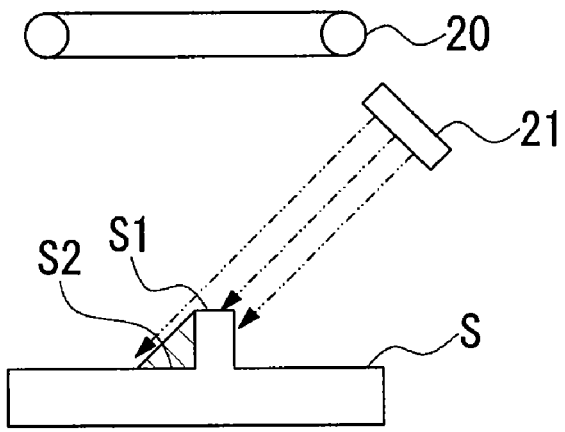
FIG. 2 is an explanatory diagram illustrating a shadow portion generated through illumination of a wide-range oblique illumination section in the embodiment.

Next, as illustrated in FIG. 2, the sample S is illuminated from thereabove in a direction oblique thereto by the wide-range oblique illumination section 21 in place of the ring illumination section 20, and the illuminated sample image is obtained as the wide-range concave-convex image data by the wide-range observation mechanism 14B. The wide-range concave-convex image data is sent to and recorded in the control section C and is displayed on the display 16*a*. The concave-convex image data is displayed alternately, side by side, or upon each other along with the reference image data on the display 16*a*.

Figure 3:
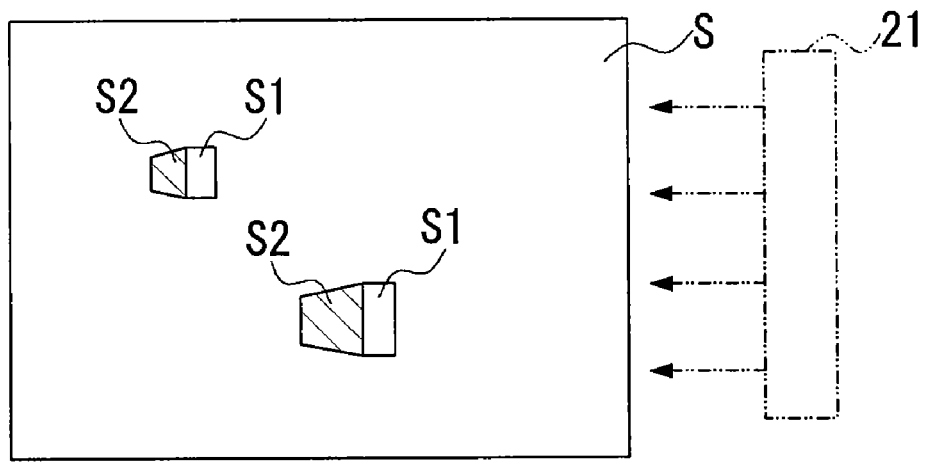
FIG. 3 is a conceptual diagram illustrating an example of a concave-convex image obtained through the illumination of the wide-range oblique illumination section in the embodiment.
Figure 4:
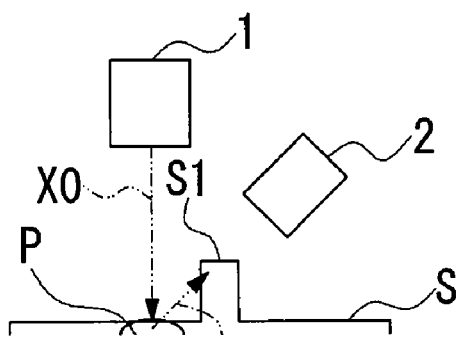
FIG. 4 is an explanatory diagram illustrating a case where an X-ray generated at an irradiation point is absorbed by a convex portion of a sample and does not reach an X-ray detector in a conventional example of the X-ray analysis apparatus and the X-ray analysis method according to the present invention.

Further, the shadow portion specification processing section 22 of the control section C performs image processing such as difference processing in which the obtained reference image data is compared with the concave-convex image data, and thus, as illustrated in FIG. 3, performs image recognition of shadow portions S2 generated by illumination of the wide-range oblique illumination section 21 to identify the shadow portions S2 as the area incapable of being analyzed. Moreover, the shadow portion specification processing section 22 records a position of the area incapable of being analyzed as the information on the area incapable of being analyzed, outputs the position to the display 16*a*, and specifies the position on the display 16*a* so as to be easily recognized by the measurer.

Next, the measurer inputs and designates the irradiation point P for analysis. On this occasion, when the specified irradiation point P is within the identified area incapable of being analyzed, in the case of manual setting, the warning mechanism 23 causes a warning light (display a warning) to blink or generates an alarming beep (generates a warning beep) based on the information on the area incapable of being analyzed. As a result, the measurer can measure another point capable of being analyzed by bringing the irradiation point P out of the area incapable of being analyzed. When the irradiation point P located in an area other than the area incapable of being analyzed is designated, the control section C drives the sample stage 10 in accordance with an operation of the measurer to move the irradiation point P of the sample S directly below the X-ray tubular bulb 11. That is, the irradiation point P is set in the area other than the area incapable of being analyzed, and the primary X-ray X1 is irradiated from the X-ray tubular bulb 11 to the sample S, with the result that the generated characteristic X-ray and scattered X-ray can be detected by the X-ray detector 12.

After the measurement of all points located in the area other than the area incapable of being analyzed, the measurer drives the rotatable stage section 10*b* manually to rotate the sample S by, for example, 180 degrees, and changes the detection direction of the X-ray detector 12. Then, the measurer sets the irradiation point P in the region which has been the area incapable of being analyzed before direction change, whereby the measurement can be performed again. In this case, the detection direction of the X-ray detector 12 is changed due to the rotation of the rotatable stage section 10*b*, and hence the characteristic X-ray and scattered X-ray generated at the irradiation point P can be emitted to the X-ray detector 12 without being interrupted by a convex portion S1.

On the other hand, in the case of automatic setting, the detection direction control section 24 of the control section C automatically controls the sample stage 10 based on the information on the area incapable of being analyzed and changes the detection direction of the X-ray detector 12 with respect to the sample S into a direction in which the irradiation point P does not fall within a shadow portion when the designated irradiation point P is located within the identified area incapable of being analyzed. For example, the rotatable stage section 10*b* is driven by the detection direction control section 24 to rotate the sample S by 180 degrees and changes its direction, whereby the irradiation point P is set in the area which has been the area incapable of being analyzed before direction change for performing automatic measurement. In this case, as in the case of the manual setting, the detection direction of the X-ray detector 12 is changed due to the rotation of the rotatable stage section 10*b*, and thus the characteristic X-ray and scattered X-ray generated at the irradiation point P can be emitted to the X-ray detector 12 without being interrupted by the convex portion S1. It should be noted that, also in the case of the automatic setting, setting may be made so that the warning is given by the warning mechanism 23.

In the case of performing the narrow-range observation, the sample stage 10 is driven to move the sample S directly below the X-ray tubular bulb 11. In this state, the sample S is illuminated by the coaxial illumination section 18 and the mirrors 13a from thereabove in the direction perpendicular thereto, and at the same time, the illuminated sample image is obtained as narrow-range reference image data by the narrow-range observation mechanism 14A. The narrow-range reference image data is sent to and recorded in the control section C and is also displayed on the display 16a.

Next, the sample S is illuminated by the narrow-range oblique illumination section 19 in place of the coaxial illumination section 18 from thereabove in a direction oblique thereto, and also the illuminated sample image is obtained as narrow-range concave-convex image data by the narrow-range observation mechanism 14A. The narrow-range concave-convex image data is sent to and recorded in the control section C and is also displayed on the display 16a. Further, the shadow portion specification processing section 22 of the control section C performs image processing such as difference processing in which the obtained reference image data is compared with the concave-convex image data, to thereby perform image recognition of the shadow portions S2 generated by illumination of the narrow-range oblique illumination section 19 and identifies the shadow portions S2 as the area incapable of being analyzed. Moreover, the shadow portion specification processing section 22 records the position of the area incapable of being analyzed as the information on the area incapable of being analyzed, outputs the position to the display 16a, and specifies the position on the display 16a so as to be easily recognized by the measurer. After that, analysis is made based on the manual setting and the automatic setting as in the case of the wide-range observation.

As described above, in this embodiment, the narrow-range illumination mechanism 13A and the wide-range illumination mechanism 13B include the narrow-range oblique illumination section 19 and the wide-range oblique illumination section 21 in which the optical axis of the illumination light is set toward the irradiation point P at the time of illumination in the same direction as the direction linking the irradiation point P with the X-ray detector 12 at the time of detection, respectively. Therefore, the shadow portion S2 corresponding to a concave-convex portion of the sample S by the illumination of the narrow-range oblique illumination section 19 and the wide-range oblique illumination section 21 can be generated and specified as the area incapable of being analyzed. That is, the shadow portion S2 is nearly equal to the area incapable of being analyzed, in which the X-ray generated at the irradiation point P at the time of detection cannot reach the X-ray detector 12 due to the concave-convex portion. When the shadow portion S2 is provided to the measurer as a visible light image, the area incapable of being analyzed can be easily specified.

In the case where the X-ray is inappropriately detected due to the concave-convex portion of the sample S, the measurer becomes capable of easily judging through the specification of the area incapable of being analyzed that an inappropriate measurement result is obtained because of a decrease in signal amount of the X-ray, with the result that erroneous determination can be prevented. For example, when a harmful substance is included, determination thereof can be made easily.

Further, the shadow portion specification processing section 22 identifies the shadow portion S2 generated by the illumination light as the area incapable of being analyzed based on the concave-convex image through image processing and also outputs its position as the information on the area incapable of being analyzed, with the result that an image of the shadow portion S2 is recognized through image processing to be automatically identified and specified. In addition, various kinds of analysis processing or analysis operations can be made based on the output information on the area incapable of being analyzed. In particular, the shadow portion specification processing section 22 identifies the area incapable of being analyzed through image processing such as difference processing in which the concave-convex images generated by the narrow-range oblique illumination section 19 and the wide-range oblique illumination section 21 are compared with the reference images generated by the coaxial illumination section 18 and the ring illumination section 20, which have illumination in directions different from one another, with the result that the area incapable of being analyzed can be identified more accurately.

In the case of the manual setting, the warning mechanism 23 displays warning or generates a warning beep based on the information on the area incapable of being analyzed if the irradiation point P is set in the area incapable of being analyzed to be measured, and hence the measurer does not need to perform unnecessary analysis operation for the area incapable of being analyzed. Accordingly, an analysis operation can be performed efficiently. As to the area incapable of being analyzed in which warning is displayed or a warning beep is generated, there can be taken a measure in which the direction of the sample S is changed and reset for remeasurement.

On the other hand, in the case of the automatic setting, the detection direction control section 24 controls the sample stage 10 based on the information on the area incapable of being analyzed and changes a positional relationship between the sample S and the X-ray detector 12 in a direction in which the irradiation point P does not fall within the shadow portion S2, with the result that the point which falls within the shadow portion S2 can also be measured automatically through change of the positional relationship between the sample S and the X-ray detector 12.

It should be noted that the technical scope of the present invention is not limited to the embodiment described above, and various modifications can be made without departing from the gist of the present invention.

For example, the description has been made on the energy dispersive fluorescent X-ray analysis apparatus in this embodiment, but the present invention is applicable to other analysis system such as a wavelength dispersive fluorescent X-ray analysis apparatus or an SEM-EDS in which an electron beam is used as a radiation beam to be irradiated.

Further, the analysis is performed by causing the sample chamber to be in a decompressed atmosphere in the embodiment described above, but may be performed in a state other than a vacuum (decompressed) atmosphere.

What is claimed is:
1. An X-ray analysis apparatus, comprising:
a radiation source for irradiating an arbitrary irradiation point located on a sample with a radiation beam;
an X-ray detector for detecting a characteristic X-ray and a scattered X-ray radiated from the sample and outputting a signal containing energy information on the characteristic X-ray and the scattered X-ray;

an illumination mechanism for emitting an illumination light to the sample to illuminate the sample; and an observation mechanism for obtaining an illumination image of the sample, which is illuminated with the illumination light, as image data, wherein the illumination mechanism includes a concave-convex illumination section in which an optical axis of the illumination light at a time of the illuminating is set toward the irradiation point in the same direction as a direction linking the irradiation point with the X-ray detector at a time of the detecting.

2. An X-ray analysis apparatus according to claim 1, further comprising a shadow portion specification processing section for identifying a shadow portion generated by the illumination light of the concave-convex illumination section as an area incapable of being analyzed through image processing based on a concave-convex image, and outputting a position thereof as information on the area incapable of being analyzed, wherein the observation mechanism records the illumination image of the sample, which is illuminated with the illumination light of the concave-convex illumination section, as the concave-convex image.

3. An X-ray analysis apparatus according to claim 2, wherein:

the illumination mechanism includes a reference illumination section in which the optical axis of the illumination light at the time of the illuminating is set toward the irradiation point in the same direction as an irradiation direction of the radiation beam at the time of the detecting;

the observation mechanism records the illumination image of the sample, which is illuminated with the illumination light of the reference illumination section, as a reference image; and the shadow portion specification processing section identifies the area incapable of being analyzed through image processing in which the concave-convex image is compared with the reference image.

4. An X-ray analysis apparatus according to claim 2, further comprising a warning mechanism for one of displaying warning and generating a warning beep based on the information on the area incapable of being analyzed when the irradiation point is set in the area incapable of being analyzed.

5. An X-ray analysis apparatus according to claim 2, further comprising:

a moving mechanism capable of relatively moving a position of the sample and a position of the concave-convex illumination section; and a detection direction control section for controlling the moving mechanism, when the irradiation point is set in the area incapable of being analyzed, based on the information on the area incapable of being analyzed, to change a detection direction of the X-ray detector with respect to the sample into a direction in which the irradiation point becomes a portion other than the shadow portion.

6. An X-ray analysis method of irradiating an arbitrary irradiation point located on a sample with a radiation beam by a radiation source, detecting a characteristic X-ray and a scattered X-ray radiated from the sample by an X-ray detector, and outputting a signal containing energy information on the characteristic X-ray and the scattered X-ray, the X-ray analysis method comprising:

illuminating the sample by emitting an illumination light to the sample by an illumination mechanism before irradiating with the radiation beam; and obtaining an illumination image of the sample, which is illuminated with the illumination light, as image data by an observation mechanism, wherein the illuminating the sample comprises setting an optical axis of the illumination light at a time of the illuminating toward the irradiation point in the same direction as a direction linking the irradiation point with the X-ray detector at a time of the detecting by a concave-convex illumination section included in the illumination mechanism, to illuminate the sample.

* * * * *